United States Patent [19]
Bannister et al.

[11] Patent Number: 5,859,279
[45] Date of Patent: Jan. 12, 1999

[54] COMPOUND AND PROCESS

[75] Inventors: Robin Mark Bannister; Graham Evans, both of Cambridge, United Kingdom

[73] Assignee: Darwin Discovery Limited, United Kingdom

[21] Appl. No.: 926,644

[22] Filed: Sep. 10, 1997

Related U.S. Application Data

[60] Provisional application No. 60/028,624, Oct. 28, 1996.

[30] Foreign Application Priority Data

Sep. 10, 1996 [GB] United Kingdom ................. 96188354

[51] Int. Cl.$^6$ ................................................. C07C 255/33
[52] U.S. Cl. ............................................ 558/404; 558/408
[58] Field of Search ...................... 558/404, 408

[56] References Cited

U.S. PATENT DOCUMENTS 4,940,780  7/1990  Seitz Werner et al. .
5,247,119  9/1993  Fowler et al. ........................... 558/390

FOREIGN PATENT DOCUMENTS 0165322  12/1985  European Pat. Off. .
1367677   9/1974  United Kingdom .

*Primary Examiner*—Brian M. Burn
*Attorney, Agent, or Firm*—Saliwanchik, Lloyd & Saliwanchik

[57] ABSTRACT

A process for the preparation of a compound of formula (VI), optionally in enantiomerically-enriched form (R or S), comprises chemoselective reduction of a novel compound of formula (V), wherein $Ar^1$ and $Ar^2$ are independently selected from optionally-substituted aromatic or heteroaromatic groups having upto 20 C atoms, Ak is $C_{1-20}$ alkyl, and R is H or $C_{1-20}$ alkyl.

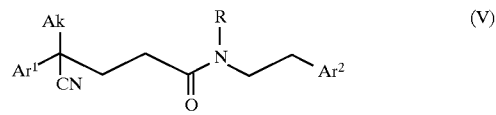

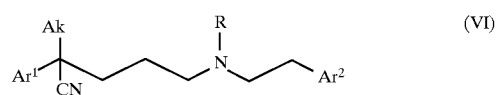

10 Claims, No Drawings

COMPOUND AND PROCESS

CROSS-REFERENCE TO RELATED APPLICATION

This application claims the benefit of U.S. Provisional Application No. 60/028,624, filed Oct. 28, 1996.

FIELD OF THE INVENTION

This invention relates to novel compounds and their use in the manufacture of enantiomerically-enriched verapamil and related compounds.

BACKGROUND OF THE INVENTION

Verapamil (I) is presently in clinical use as the racemate and is used extensively for the treatment of hypertension. The opposite enantiomers of verapamil have different biological activities. The (S)-enantiomer (levoverapamil) has the majority of the calcium channel antagonist activity (DE-A-2059923) whilst the (R)-enantiomer (dextroverapamil) differs in having sodium channel and other cell-pump actions in addition to higher bioavailability, with slower clearance rate. These differences may be of clinical significance, for example, the (R)-enantiomer may be of benefit for the reversal of multidrug resistance in cancer chemotherapy (see Eliason, Int. J. Cancer (1990) 46: 113); in this case hypotensive action by admixture with the (S)-enantiomer would be undesirable.

Thus there is a requirement for efficient manufacturing processes to produce single enantiomer or enantiomerically-enriched forms of the compound verapamil and analogues thereof. This is a challenging endeavour since construction of the quaternary chiral centre with high asymmetric induction is difficult. Several synthetic routes to such compounds have been published but for a variety of reasons most are unsuitable for preparation on a large scale.

For example, the synthesis of (S)-verapamil commencing from (S)-1,2-propanediol entails 11 steps, only 3 of which are used to create permanent skeletal bonds; see Theodore and Nelson, J. Org. Chem. (1987) 52: 1309. Of the shorter routes proceeding via classical resolution are processes disclosed in WO-A-9729081, which involve resolution of 4-cyano-4-(3,4-dimethoxyphenyl)-5-methyl hexanoic acid (II; verapamilic acid). Such processes are potentially advantageous over the resolution of verapamil itself (disclosed in DE-A-3723684 and WO-A-9316035) due to better atom utilisation and lower waste levels. Literature methodology for the conversion of enantiomerically-enriched (II) to verapamil (1), and corresponding processes for analogues, invariably entails reduction of (II) to either the enantiomerically-enriched alcohol (III) or the enantiomerically-enriched aldehyde (IV).

Proceeding via alcohol (III) involves conversion to either an O-sulphonyl derivative or an alkyl halide, and subsequent amination to verapamil (I), which may require elevated temperatures (see GB 1367677), prolonged reaction times (see Theodore and Nelson, as above), or the use of the hazardous solvent hexamethylphosphoramide (see U.S. Pat. No. 4,940,780). Proceeding via aldehyde (IV), an a large scale from (II), requires two operations, either reduction-oxidation via alcohol (III) or acid chloride formation, and then a Rosenmund reaction. Racemic analogues of (IV) are available without recourse to this awkward adjustment of oxidation levels, but the protocols used, for instance as described in DE-A-2631222, are not suitable for preparing enantiomerically-enriched compounds.

For the above reasons it is desirable to establish a more streamlined protocol for the conversion of enantiomerically-enriched (II) to enantiomerically-enriched verapamil (I).

SUMMARY OF THE INVENTION

According to a first aspect of the present invention, a novel compound, optionally in enantiomerically-enriched form (R or S) has the formula (V), below, wherein $Ar^1$ and $Ar^2$ are independently selected from optionally-substituted aromatic or heteroaromatic groups having upto 20 C atoms, Ak is $C_{1-20}$ alkyl, and R is H or $C_{1-20}$ alkyl.

According to a second aspect of the present invention, a process for the preparation of a compound of formula (VI), below, optionally in enantiomerically-enriched form (R or S) comprises chemoselective reduction of a compound of formula (V), as defined above. It is surprising that, in this process, little or no reduction of the nitrile functionality is observed, since it is commonly documented that amide and nitrile functional groups have similar susceptibility to reducing agents; see, for instance, J. March, Advanced Organic Chemistry, $4^{th}$ ed., Wiley (1992) Wiley, p. 1206–1209.

DESCRIPTION OF THE INVENTION

In the present Application, by enantiomerically-enriched typically we mean that one enantiomer (R or S), is present in an excess compared to the other enantiomer of at least 50%, preferably at least 70%, and more preferably higher, eg. at least 80% or 90%. This term, therefore, is intended also to cover enantiomerically-pure, or single isomer, materials.

The compounds of formula (V) may be prepared by reaction of a suitable carboxylic acid with a suitable primary or secondary amine, under standard reaction conditions.

The substituents of compound (V) have been defined above. When R is alkyl, it may be the same or different to the Ak group. Preferably both R and Ak are independently selected from $C_{1-12}$ alkyl, and R is more preferably methyl.

In one particularly preferred embodiment of the invention, verapamil (I) is prepared by reduction of compound (V) in which $Ar^1$ and $Ar^2$ are both 3,4-dimethoxyphenyl, Ak is isopropyl, and R is methyl. In another particularly preferred embodiment, verapamil is prepared by reduction of compound (V) in which $AR^1$ and $AR^2$ are both 3,4-dimethoxyphenyl, Ak is isopropyl, and R is H, followed by N-methylation; omission of the N-methylation step provides a route to norverapamil, optionally in enantiomerically-enriched form.

A number of reagents are suitable for effecting the desired chemoselective reduction of compound (V), including metal hydride reagents and borane-based reagents. Suitable metal hydride reagents include aluminohydride reagents such as lithium aluminium hydride. Suitable borane-based reagents include preformed complexes of borane with either dimethyl sulphide or tetrahydrofuran. Alternatively, and more economically, borane may be generated in situ, typically by the reaction of sodium borohydride with an acidic reagent such as hydrogen chloride.

A particular advantage of the present invention, for the preparation of enantiomerically-enriched verapamil, is that an intermediate, enantiomerically-enriched in the R- or S-enantiomer, containing the entire verapamil skeleton can be prepared by reaction of enantiomerically-enriched 4-cyano-4-(3,4-dimethoxyphenyl)-5-methylhexanoic acid (II; verapamilic acid) and a homoveratrylamine (VII, R=$C_{1-20}$ alkyl), without awkward adjustment of oxidation level in the former. Moreover, coupling of compounds (II) and (VII) to prepare an amide (VI) may be achieved by condensation under mild conditions in which approximately equimolar quantities of reactants can be used.

The present invention is further illustrated by the following Examples.

EXAMPLES

Preparation of Amides

Example 1

4-cyano-4-(3,4-dimethoxyphenyl)-5,N-dimethyl-N-(2-phenylethyl) hexanamide 5.0 g of 4-cyano-4-(3,4-dimethoxy-phenyl)-5-methyl hexanoic acid (0.0172 mol) and 2.32 g, 2.50 ml of N-methylphenethylamine (0.0172 mol) in the presence of 30 mg of 3-nitrophenylboronic acid (~1 mol %) were set to reflux in 80 mls of toluene. The formed water was removed by use of Dean and Stark apparatus. After overnight heating GC/MS analysis indicated complete conversion of the acid (RT=25.07 mins) to the amide (RT=38.33 mins, m/z 408). After allowing to cool, the toluene solution was washed with 100 ml of 1.0N NaOH solution. The basic aqueous layer was re-extracted with 100 ml of toluene. The organic layers were combined and washed with 100 ml of water. The organic layers were dried over $MgSO_4$, filtered and evaporated to dryness giving the amide in essentially quantitative yield as a yellow/green coloured oil. IR (liq film) ν (C=0)=1649.9 $cm^{-1}$.

Example 2

4-cyano-4-(3,4-dimethoxyphenyl)-N-[2-(3,4-dimethoxy-phenyl) ethyl]-5,N-dimethylhexanamide Using the procedure of Example 1, 5.0 g of 4-cyano-4-(3,4-dimethoxyphenyl)-5-methyl hexanoic acid (0.0172 mol) and 3.35 g, 3.17 ml of N-methylhomoveratrylamine (0.0172 mol) were coupled in the presence of 30 mg of 3-nitrophenylboronic acid (~1 mol %). This gave after work-up 7.17 g (89.1%) of a yellow/orange coloured oil. Addition of 10 mls of TBME and 5 mls petrol (60–80) effected crystallisation to give 5.81 g (72.2%) of a beige coloured solid. Mp=92.1° C. IR (KBr disc), ν(C=0)=1636.3 $cm^{-1}$.

Example 3

(S)-4-cyano-4-(3,4-dimethoxyphenyl)-N-[2-(3,4-dimethoxy-phenyl) ethyl]-5,N-dimethylhexamide (S)-4-cyano-3-(3,4-dimethoxyphenyl)-5-methylhexanoic acid (347.5 g, 1.19 mol) was reacted with N-methylhomoveratrylamine (255.8 g, 1.1 eq) in xylene (1.75 l) at reflux, in the presence of 3-nitrophenylboronic acid (0.99 g 0,005 eq) as catalyst. The water of reaction was removed continuously through use of a Dean-Stark trap. After a total of 24 hours at reflux the reaction was substantially complete, as judged both by hplc analysis and by water removal (>98% of theory). The reaction mixture was then worked up by addition of water (500 ml) and then adjustment of pH to 1.5 with hydrochloric acid (35%, ca 20 ml), to remove unreacted amine. The lower aqueous phase was separated, and the organics given a wash at pH 1.5, then an alkaline wash (pH 11), to remove unreacted verapamilic acid (4.8 g of 47% w/w NaOH required). After a final water wash, the organic phase was partially concentrated under vacuum to a weight of 732 g. Crystallisation was induced after dilution of the resulting oily residue with xylene; the product was isolated in 88% yield by filtration, washing with xylene, and drying. Mp=95.5° C.

Reductions of Amides i) Reductions using Borane Reagents

Example 4

Reduction of 4-cyano-4-(3,4-dimethoxyphenyl)-5,N-dimethyl-N-(2-phenylethyl) hexanamide 1.50 g (3.68 mol) 4-cyano-4-(3,4-dimethoxyphenyl)-5,N-dimethyl-N-(2-phenylethyl)hexanamide was taken up in 10 ml of dry THF under nitrogen at 0° C. To this solution was added 0.350 g, 0.440 ml of borane dimethyl sulphide complex (4.60 mmol) dropwise over a 5 minute period. GC/MS analysis indicated that after stirring at room temperature for 18 hours 59% conversion to the amine 4-cyano-4-(3,4-dimethoxyphenyl)-5,N-dimethyl-N-(2-phenylethyl) hexylamine had occurred. After 2 hours reflux this improved to 71%. When 2 equivalents of $BH_3$.DMS, were used after 3 hours at room temperature the conversion to the amine was improved to 87%. The amine was converted to its oxalate salt Mp=113.6°C.

Example 5

Reduction of 4-cyano-4-(3,4-dimethoxyphenyl)-N-[2-3,4-dimethoxyphenyl) ethyl]-5,N-dimethylhexanamide Using the procedure of Example 4, 2 eq of BH3.DMS, 1.0 g of 4-cyano-4-(3,4-dimethoxyphenyl)-N-[(2-(3,4-dimethoxyphenyl) ethyl]-5, N-dimethyl-hexanamide (2.14 mmol) was taken up in 10 ml of dry THF at 0° C. under nitrogen. Addition of 0.325 g, 0.41 ml of borane dimethyl sulphide complex (4.28 mmol) via syringe. After 5 hours stirring at room temperature GC/MS analysis indicated full conversion to verapamil, which was converted to its oxalate salt Mp=140.0° C.

Example 6

Reduction of 4-cyano-4-(3,4-dimethoxyphenyl)-N-[2-(3,4-dimethoxyphenyl) ethyl]-5,N-dimethylhexamide with borane generated in situ 5.0 g of the amide (10.7 mol) and 1.01 g of sodium borohydride (26.7 mmol) were suspended in 15 ml of 1,2-dimethoxyethane at 0° C. under nitrogen. To this suspension was added 35 ml of a 0.77M solution of gaseous HCl in 1,2-dimethoxyethane. After 4 hours stirring at room temperature the reaction was shown to be complete by GC/MS. The reaction was quenched by addition of 25 ml of 6.0M hydrochloric acid. After extractive work-up, 5.1 g of crude verapamil hydrochloride was obtained, which was recrystallised from 50 ml of ethyl acetate to give a white solid, m.p. 129.3° C.

Example 7

Reduction of (S)-4-cyano-4-(3,4-dimethoxyphenyl)-N-[2-(3,4-dimethoxyphenyl) ethyl]-5,N-dimethylhexamide with borane generated in situ Using a similar procedure to that described in Example 8, 23 ml of a 4.17M solution of gaseous HCl in 1,2- dimethoxyethane was added to a suspension of 17.9 g of the single enantiomer amide (38.3 mmol) and sodium borohydride (3.62 g, 95.8 mmol) in 100 ml of 1,2-dimethoxyethane. Reaction was complete after 1.25 hours. Quenching with 50 ml of 6.0K hydrochloric acid, followed by extractive work-up and recrystallisation (100 ml of isopropyl acetate) gave 13.1 g of (S)-verapamil hydrochloride.

ii) Reductions using Lithium Aluminium Hydride

Example 8

Reduction 4-cyano-4-(3,4-dimethoxyphenyl)-5,N-dimethyl-N-(2-phenylethyl) hexanamide Using a similar procedure to that described in Examples 4 and 5; 1.0 g of the amide (2.45 mmol) was taken up in 10 ml of dry THF at 0° C. under nitrogen. To this solution was added 2.70 ml of 1.0M LiAlH$_4$ in THF (2.70 mmol) via syringe. Stirring was continued at room temperature for 18 hours. Addition of 5 ml of ethyl acetate and subsequent aqueous work-up gave 0.78 g (78%) of a yellow green coloured oil (4-cyano-4-(3,4-dimethoxyphenyl)-5,N-dimethyl-N-(2-phenylethyl)hexylamine), which was converted to its oxalate salt.

Example 9

Reduction of 4-cyano-4-(3,4-dimethoxyphenyl)-N-[2-(3,4-dimethoxyphenyl ethyl]-5,N-dimethylhexanamide Using the procedure of Example 6, 1.0 g of the amide (2.14 mmol) in 10 ml of dry THF was added 2.35 ml of 1.0M LiAlH$_4$ in THF (2.35 mmol). After overnight stirring the reaction was quenched by addition of 5 ml of ethyl acetate. Standard work-up gave 0.758 g (78.0%) of yellow/green coloured oil (verapamil), which was converted to its oxalate salt.

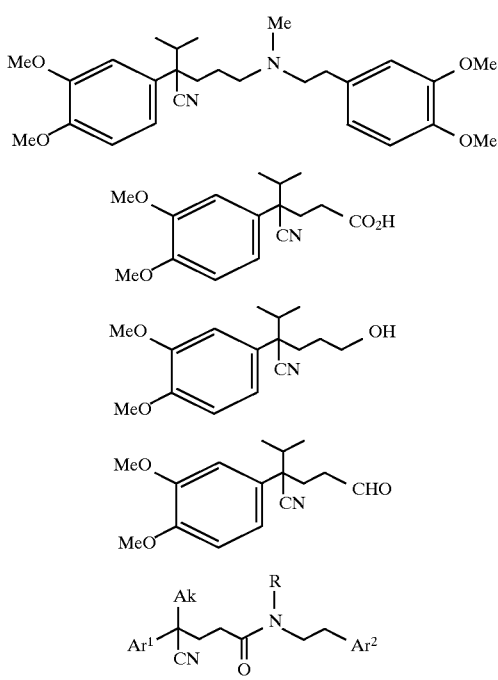

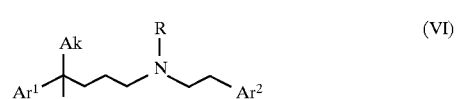

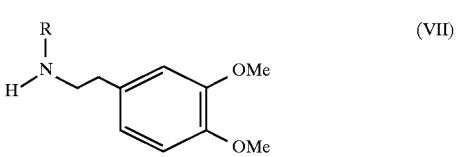

We claim:

1. A compound of formula (V),

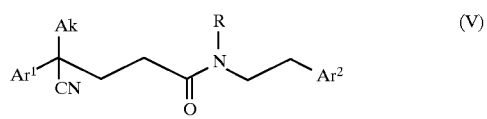

wherein $AR^1$ and $AR^2$ are independently selected from optionally-substituted aromatic groups having up to 20 carbon atoms, Ak is $C_{1-20}$ alkyl, and R is H or $C_{1-20}$ alkyl.

2. The compound, according to claim 1, in enantiomerically-enriched form (R or S).

3. The compound, according to claim 1, wherein $AR^1$ and $AR^2$ are each 3,4-dimethoxyphenyl, Ak is isopropyl, and R is H or methyl.

4. A method for preparing a compound of the formula (VI)

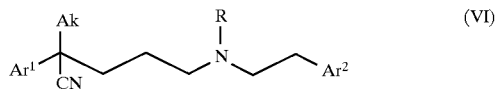

optionally in enantiomerically-enriched form (R or S), wherein said method comprises chemoselective reduction of a compound of formula (V) as defined in claim 1.

5. The method, according to claim 4, wherein the reduction is effected by a metal hydride reagent.

6. The method, according to claim 4, wherein the reduction is effected by a borane-based reagent.

7. The method, according to claim 4, for preparing verapamil, optionally in enantiomerically-enriched form (R or S), wherein Ar$^1$, Ar$^2$, and Ak are each 3,4-dimethoxyphenyl, Ak is isopropyl; and R is methyl.

8. A method for preparing verapamil, optionally in enantiomerically-enriched form (R or S), comprising preparing a compound of formula (VI) by the method of claim 4, wherein Ar$^1$, Ar$^2$, and Ak are each 3,4-dimethoxyphenyl, Ak is isopropyl, and R is H; and subjecting compound (VI) to N-methylation.

9. The compound, according to claim 1, wherein said optionally-substituted aromatic group is a phenyl group.

10. The method, according to claim 4, wherein said optionally-substituted aromatic group is a phenyl group.

* * * * *

UNITED STATES PATENT AND TRADEMARK OFFICE
CERTIFICATE OF CORRECTION

PATENT NO. : 5,859,279
DATED : January 12, 1999
INVENTOR(S) : Robin Mark Bannister and Graham Evans It is certified that error appears in the above-identified patent and that said Letters Patent is hereby corrected as shown below:

Column 2, lines 45-46: "$AR^1$ and $AR^2$" should read --$Ar^1$ and $Ar^2$--.

Column 6, line 23: (claim 1): "$AR^1$ and $AR^2$" should read --$Ar^1$ and $Ar^2$--; and Column 6, lines 28-29 (claim 3): "$AR^1$ and $AR^2$" should read --$Ar^1$ and $Ar^2$--.

Signed and Sealed this

Eighteenth Day of May, 1999

*Attest:*

Q. TODD DICKINSON

*Attesting Officer*     *Acting Commissioner of Patents and Trademarks*